(12) United States Patent
Reddy et al.

(10) Patent No.: US 9,083,129 B2
(45) Date of Patent: Jul. 14, 2015

(54) MULTIPOLAR LEAD EVALUATION DEVICE

(75) Inventors: G. Shantanu Reddy, Minneapolis, MN (US); Bruce A. Tockman, Scandia, MN (US); Christopher A. Fuhs, Roseville, MN (US); Bryan Swackhamer, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1040 days.

(21) Appl. No.: 13/179,162

(22) Filed: Jul. 8, 2011

(65) Prior Publication Data

US 2012/0019260 A1 Jan. 26, 2012

Related U.S. Application Data

(60) Provisional application No. 61/364,269, filed on Jul. 14, 2010.

(51) Int. Cl.
| *A61N 1/372* | (2006.01) |
| *H01R 24/58* | (2011.01) |
| *A61N 1/05* | (2006.01) |
| *A61N 1/08* | (2006.01) |

(52) U.S. Cl.
CPC ............... *H01R 24/58* (2013.01); *A61N 1/372* (2013.01); *A61N 1/056* (2013.01); *A61N 1/08* (2013.01); *H01R 2201/12* (2013.01)

(58) Field of Classification Search
CPC ......... A61N 1/08; A61N 1/37; A61N 1/3704; A61N 1/372; A61N 1/375; A61N 1/3752; A61N 1/3754; A61N 1/056
USPC .............................................. 607/27, 37, 116
See application file for complete search history.

(56) References Cited

U.S. PATENT DOCUMENTS

| 4,209,019 A | 6/1980 | Dutcher et al. |
| 4,744,371 A | 5/1988 | Harris |
| 5,275,620 A | 1/1994 | Darby et al. |
| 5,334,045 A | 8/1994 | Cappa et al. |
| 5,354,326 A | 10/1994 | Comben et al. |
| 5,535,745 A | 7/1996 | Ingram et al. |
| 5,557,210 A | 9/1996 | Cappa et al. |
| 5,679,022 A | 10/1997 | Cappa et al. |
| 5,782,841 A | 7/1998 | Ritz et al. |
| 5,782,892 A | 7/1998 | Castle et al. |
| 5,931,861 A | 8/1999 | Werner et al. |
| 6,038,479 A | 3/2000 | Werner et al. |

(Continued)

FOREIGN PATENT DOCUMENTS

| WO | WO0056402 A1 | 9/2000 |
| WO | WO2004101068 A1 | 11/2004 |
| WO | WO2011082160 A2 | 7/2011 |

OTHER PUBLICATIONS

International Search Report and Written Opinion issued in PCT/US2010/062215, mailed Jan. 31, 2012, 18 pages.

*Primary Examiner* — Allen Porter, Jr.
(74) *Attorney, Agent, or Firm* — Faegre Baker Daniels LLP (57) ABSTRACT

A multipolar lead evaluation device may be configured to easily permit electrical contact to be made between a pacing system analyzer and the terminal pin and each of the terminal contacts of an implantable lead without damaging the implantable lead. Alligator clips may be used to secure electrical conductors from the pacing system analyzer to spring contact clips disposed within the lead evaluation device.

12 Claims, 7 Drawing Sheets

(56) References Cited

U.S. PATENT DOCUMENTS

| | | |
|---|---|---|
| 6,038,481 A | 3/2000 | Werner et al. |
| 6,162,101 A | 12/2000 | Fischer et al. |
| 6,192,278 B1 | 2/2001 | Werner et al. |
| 6,343,233 B1 | 1/2002 | Werner et al. |
| 6,415,168 B1 | 7/2002 | Putz |
| 6,463,334 B1 | 10/2002 | Flynn et al. |
| 6,580,948 B2 | 6/2003 | Haupert et al. |
| 7,130,699 B2 | 10/2006 | Huff et al. |
| 2003/0123027 A1 | 7/2003 | Amir et al. |
| 2004/0215302 A1 | 10/2004 | Sage et al. |
| 2004/0230268 A1* | 11/2004 | Huff et al. .............. 607/116 |
| 2005/0177199 A1 | 8/2005 | Hansen et al. |
| 2006/0258193 A1 | 11/2006 | Hoecke et al. |
| 2008/0015668 A1 | 1/2008 | Soukup |
| 2008/0248696 A1 | 10/2008 | Kast et al. |
| 2008/0255630 A1 | 10/2008 | Arisso et al. |
| 2011/0160824 A1 | 6/2011 | Ware et al. |

* cited by examiner

MULTIPOLAR LEAD EVALUATION DEVICE

CROSS-REFERENCE TO RELATED APPLICATION

This application claims the benefit under 35 U.S.C. §119(e) to U.S. Provisional Patent Application No. 61/364,269, filed on Jul. 14, 2010, entitled "MULTIPOLAR LEAD EVALUATION DEVICE," which is incorporated herein by reference it its entirety

TECHNICAL FIELD

The present invention relates generally to implantable medical devices. More specifically, the present invention relates to devices, systems, and methods for installing and testing multi-conductor electrical leads within a patient's body.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing some other desired function within the body. Such leads often include one or more electrodes for sensing and delivering electrical stimuli and a proximal, terminal end which is connected to the pulse generator. The terminal end of the lead includes one or more electrical contacts that are electrically connected to the electrodes on the terminal end of the lead via a number of conductors.

In certain applications, the leads are tested for proper positioning and function as part of the implantation process and prior to being connected to the pulse generator, allowing the implanting physician to evaluate pacing and sensing performance prior to concluding that the particular lead position is suitable. During the testing process, for example, a Pacing System Analyzer (PSA) may be connected to the terminal end of the lead to test the connection of the conductor end of the lead to the heart and/or to evaluate the performance of the lead. To facilitate connection of the PSA to the lead, a lead implant tool can be temporarily coupled to the terminal end of the lead, allowing the conductors of the PSA to be connected to the electrical contacts on the terminal end of the lead.

More recent trends in lead designs have focused on the development of lead connectors with up to four electrical contacts. The terminal ends of such leads are not significantly different in size from previous, IS-1 standard leads, which include only two terminal contacts. Many existing spring-loaded clips used for connecting the PSA to the terminal contacts are often inadequate for use with more modern lead designs, particularly due to the limited spacing between the contacts, and since the space between the contacts is sometimes used as a sealing area to ensure electrical isolation.

SUMMARY

Example 1 is a lead evaluation device that is configured for connection to a proximal portion of an implantable lead having a terminal boot, a plurality of terminal contacts and a terminal pin. The lead evaluation device includes a main body having a first side, an opposing second side and an opening configured to frictionally engage the terminal boot. A channel configured to accommodate the proximal portion of the implantable lead extends through the main body from the opening. The lead evaluation device includes a plurality of terminal contact clips coupled to the main body such that each of the plurality of terminal contact clips are positioned to releasably make electrical contact with a corresponding one of the plurality of terminal contacts when the implantable lead is disposed within the channel.

In Example 2, the lead evaluation device of Example 1, further including a clamping tab disposed along either the first side or the second side of the main body to permit temporarily fixating the lead evaluation device.

In Example 3, the lead evaluation device of Example 1 or Example 2 in which each of the plurality of terminal contact clips are biased into a relaxed configuration in which they do not extend into the channel and may be moved into a contact configuration in which they extend into the channel and contact the proximal portion of the implantable lead by placing an alligator clip onto each of the plurality of electrode contact clips.

In Example 4, the lead evaluation device of Example 2 or Example 3 in which at least one of the plurality of terminal contact clips are configured to be in contact with at least one of the terminal contacts when the lead is disposed in the channel.

In Example 5, the lead evaluation device of any of Examples 1-4 in which each of the plurality of terminal contact clips include a spring clip including an upper portion, a lower portion and an intervening hinge portion, at least one of the upper portion and the lower portion including a contact ridge for contacting an electrode.

In Example 6, the lead evaluation device of any of Examples 1-5, further including a terminal pin contact clip configured to contact the terminal pin when the implantable lead is disposed within the lead evaluation device.

In Example 7, the lead evaluation device of any of Examples 1-6 in which one or more of the plurality of terminal contact clips are disposed along the first side of the main body and one or more of the plurality of terminal contact clips are disposed along the second side of the body.

In Example 8, the lead evaluation device of Example 7 in which the first side of the main body is curved, the plurality of terminal contact clips are disposed along the first side of the body, and the terminal pin contact clip is disposed along the first side of the body.

In Example 9, the lead evaluation device of Example 8 in which the plurality of terminal contact clips each have a configuration including a relatively wider clamping portion proximate the first side of the main body and a relatively narrower terminal contact portion disposed on an opposing side of the channel from the relatively wider clamping portion.

In Example 10, the lead evaluation device of any of Examples 1-9, further including an elongate groove extending along either the first side or the second side of the main body to permit side-loading of the lead evaluation device over a stiffening member.

Example 11 is a system for testing an implantable lead within the body of a patient. The system includes an implantable lead having a terminal boot, a plurality of terminal contacts and a terminal pin, a pacing system analyzer electrically connected to a plurality of alligator clips and the lead evaluation device of any of Examples 1-10, upon which the plurality of alligator clips may be releasably attached for testing the implantable lead.

Example 12 is a lead evaluation device configured for connection to a proximal portion of an implantable lead having a terminal boot, a plurality of terminal contacts and a terminal pin. The lead evaluation device includes a main body including a curved first side and an opposing second side, a channel extending through the main body, the channel including an opening configured to frictionally engage the terminal boot, and an elongate groove extending along the second side, the elongate groove providing access to the channel for sideloading the lead evaluation device over a stiffening member. A terminal pin spring clip is disposed on the curved first side of the main body at an acute angle with respect to the channel, the terminal pin spring clip including an alligator clip engagement portion and a terminal pin contact portion that is narrower than the alligator clip engagement portion. A plurality of terminal contact clips are disposed on the curved first side of the main body, each of the plurality of terminal contact clips disposed at acute angles with respect to the channel, each of the plurality of terminal contact clips including an alligator clip engagement portion and an electrode contact portion that is narrower than the corresponding alligator clip portion.

In Example 13, the lead evaluation device of Example 12 in which the terminal pin spring clip and each of the plurality of terminal contact clips include a hinge portion, the hinge portions aligned along an arc that at least substantially matches a curvature of the curved first side.

In Example 14, the lead evaluation device of Example 12 or Example 13 in which the plurality of terminal contact clips includes three terminal contact clips.

In Example 15, the lead evaluation device of any of Examples 11-14, further including a clamping tab disposed along the second side of the main body to permit temporarily fixating the lead evaluation device.

In Example 16, the lead evaluation device of any of Examples 11-15 in which each of the plurality of terminal contact clips are biased into a relaxed configuration in which they do not extend into the channel.

In Example 17, the lead evaluation device of Example 16 in which each of the plurality of terminal contact clips may be moved into a contact configuration in which they extend into the channel and contact the proximal portion of the implantable lead by placing an alligator clip onto each of the plurality of terminal contact clips.

In Example 18, the lead evaluation device of any of Examples 11-17 in which the terminal contact portion of each of the plurality of terminal contact clips includes a contact ridge for contacting a terminal contact.

Example 19 is a system for testing an implantable lead within the body of a patient. The system includes an implantable lead having a terminal boot, a plurality of terminal contacts and a terminal pin, a pacing system analyzer electrically connected to a plurality of alligator clips, and the lead evaluation device of any of Examples 11-18, upon which the plurality of alligator clips may be releasably attached for testing the implantable lead.

Example 20 is a method of testing an implantable lead during or after implantation, the implantable lead including a terminal boot, a plurality of terminal contacts and a terminal pin. The terminal boot of the implantable lead is frictionally engaged with a lead evaluation device that includes a main body including a first side, an opposing second side and an opening configured to frictionally engage the terminal boot. A channel configured to accommodate the proximal portion of the implantable lead extends through the main body from the opening. A plurality of terminal contact clips are coupled to the main body such that each of the plurality of terminal contact clips are positioned to releasably make electrical contact with a corresponding one of the plurality of terminal contacts when the implantable lead is disposed within the channel. An alligator clip is secured onto each of the plurality of terminal contact clips, each of the alligator clips being electrically connected to a pacing system analyzer. The implantable lead is tested with the pacing system analyzer.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
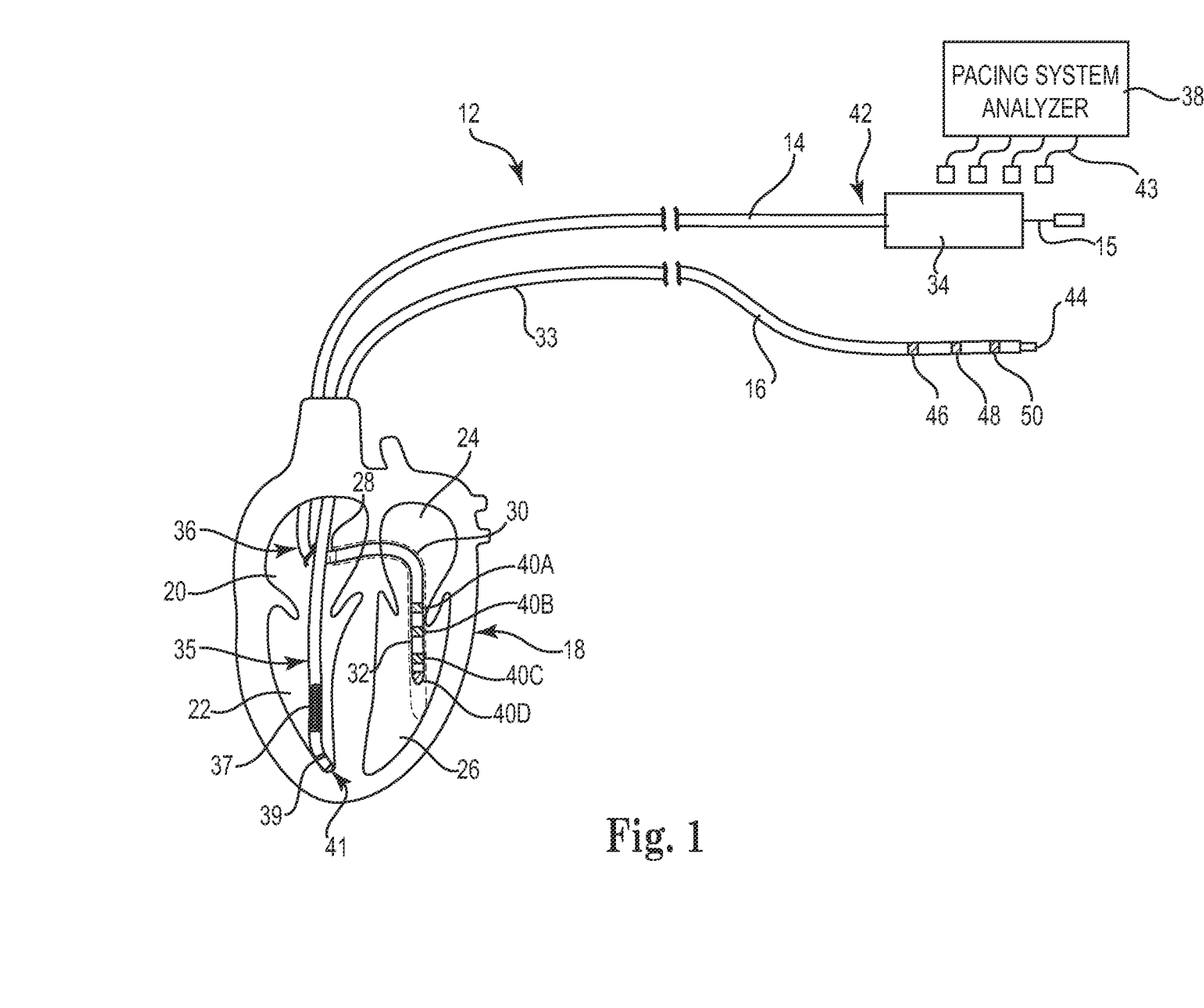
FIG. 1 is a schematic illustration of an implantable cardiac rhythm management (CRM) system according to one embodiment of the present invention in a deployed configuration.

FIG. 1 is a schematic drawing of an implantable cardiac rhythm management (CRM) system 10 according to one embodiment of the present invention, shown in a deployed state. As shown in FIG. 1, the CRM system 10 includes a cardiac lead system 12 including a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30. While not illustrated, the CRM system 10 may include a pulse generator to which the cardiac lead system 12 may be coupled. In some embodiments, the CRM system 10 may be configured for use in cardiac resynchronization therapy (CRT).

As shown in FIG. 1, the lead 14 includes a proximal portion 42 and a distal portion 36, which as shown is guided through the right atrium 20, the coronary sinus ostium 28 and the coronary sinus 30, and into the branch vessel 32 of the coronary sinus 30. The distal portion 36 further includes several electrodes 40A, 40B, 40C and 40D. In some embodiments, the distal portion 36 may include fewer electrodes or may in some cases include more than four electrodes.

The illustrated position of the lead 14 may be used for delivering a pacing and/or defibrillation stimulus to the left side of the heart 18. Additionally, the lead 14 may also be partially deployed in other regions of the coronary venous system, such as in the great cardiac vein or other branch vessels for providing therapy to the left side or right side of the heart 18.

In the illustrated embodiment, the electrodes 40A, 40B, 40C and 40D are relatively small, low voltage electrodes configured for sensing intrinsic cardiac electrical rhythms and/or delivering relatively low voltage pacing stimuli to the left ventricle 26 from within the branch vessel 32. In various embodiments, the lead 14 can include additional pace/sense electrodes for multi-polar pacing and/or for providing selective pacing site locations.

As further shown, in the illustrated embodiment, the lead 16 includes a proximal portion 33 and a distal portion 35 implanted in the right ventricle 22. In other embodiments, the CRM system 10 may include still additional leads, e.g., a lead implanted in the right atrium 20. The distal portion 35 further includes a flexible, high voltage electrode 37, a relatively low-voltage ring electrode 39, and a low voltage tip electrode 41 all implanted in the right ventricle 22 in the illustrated embodiment. The high voltage electrode 37 has a relatively large surface area compared to the ring electrode 39 and the tip electrode 41, and is thus configured for delivering relatively high voltage electrical stimulus to the cardiac tissue for defibrillation/cardioversion therapy, while the ring and tip electrodes 39, 41 are configured as relatively low voltage pace/sense electrodes. The electrodes 39, 41 provide the lead 16 with bi-polar pace/sense capabilities.

In various embodiments, the lead 16 includes additional defibrillation/cardioversion and/or additional pace/sense electrodes positioned along the lead 16 so as to provide multi-polar defibrillation/cardioversion capabilities. In one exemplary embodiment, the lead 16 includes a proximal high voltage electrode in addition to the electrode 37 positioned along the lead 16 such that it is located in the right atrium 20 (and/or superior vena cava) when implanted. Additional electrode configurations can be utilized with the lead 16. In short, any electrode configuration can be employed in the lead 16 without departing from the intended scope of the present invention.

A pulse generator is typically implanted subcutaneously within an implantation location or pocket in the patient's chest or abdomen. The pulse generator may be any implantable medical device known in the art or later developed, for delivering an electrical therapeutic stimulus to the patient suitable for treating cardiac tachyarrhythmias. In various embodiments, the pulse generator is a pacemaker, an implantable cardioverter defibrillator (ICD) or a cardiac resynchronization (CRT) device configured for bi-ventricular pacing and including defibrillation capabilities (i.e., a CRT-D device). While not shown, the pulse generator includes hardware, software, and circuitry operable as a detection/energy delivery system configured to receive cardiac rhythm signals from the lead electrode(s) 40A, 40B, 40C, 40D, 39 and 41 and also to deliver a therapeutic electrical stimulus to one or more of the electrodes 40A, 40B, 40C, 40D, 39 and 41. In various embodiments, the CRM system 10 further includes an additional lead deployed in the right atrium 20, which lead may include one or more additional electrodes sensing intrinsic cardiac signals and/or delivering electrical stimuli to the cardiac tissue within the right atrium 20.

In the illustrative embodiment depicted, the system 10 further includes a lead evaluation device 34, a stiffening member 15 such as a stylet or guidewire, and a Pacing System Analyzer (PSA) 38 that can be used for testing the lead 14 within the body. The PSA 38 may include electrical conductors 43 that may be used to electrically couple the PSA 38 to the lead 14.

During the course of the implantation procedure, to evaluate the viability of a potential fixation site, the function and location of the lead 14 can be tested by using the lead evaluation device 34 to provide electrical contact between the PSA 38 and the lead 14. In some embodiments, the lead evaluation device 34 may also be used to confirm capture in the lead 16 as well.

Such testing can be performed, for example, to verify that one or more contacts at a terminal end 42 of the lead 14 are in electrical contact with the electrodes 40A, 40B, 40C and 40D, and that the electrodes 40A, 40B, 40C and 40D are properly positioned on or within the heart 18. The PSA 38 can also be used to perform other functions, such as programming the implantable device (e.g., pulse generator) to be coupled to the implantable lead 14, and to generate any pacing pulses necessary to support the patient during the implantation process.

In some embodiments, the lead evaluation device 34, the stiffening member 15, and/or other components of the system 10 can be shipped as part of a kit already attached to an implantable lead 14. In certain embodiments, for example, the lead evaluation device 34 can be pre-loaded onto a portion of the implantable lead 14 with the stiffening member 15 pre-inserted through the lead evaluation device 34 and a portion of the lead 14. In some embodiments, as will be discussed below, the lead evaluation device 34 may be configured to permit side-loading of the lead evaluation device 34 over the stiffening member 15.

In some embodiments, the lead evaluation device 34 protects the lead connector throughout the implant procedure from electrical clips or other surgical implements. As such, the lead evaluation device 34 is typically removed just prior to the connection of the device to another implantable device such as a pulse generator. At that time, the lead evaluation device 34 is removed from the lead 14, and the lead 14 is then connected to the pulse generator.

Exemplary leads and lead connectors that can be used in conjunction with the lead evaluation device 34 can include, but are not limited to, CRT or pacing leads (e.g., including a quadripolar (e.g., IS-4 or similar) connector, or a dual-pole (e.g., IS-1 or similar) connector), ICD leads (e.g., including a quadripolar (DF-4 or similar) connector, or a lead with multiple IS-1 and/or DF-1 type connectors), and leads including additional sensing capabilities (e.g., a pressure sensing/pacing lead with a quadripolar type connector). Other types of leads and/or lead connector types can also be used in conjunction with the lead evaluation device 34, as desired.

Figure 2:
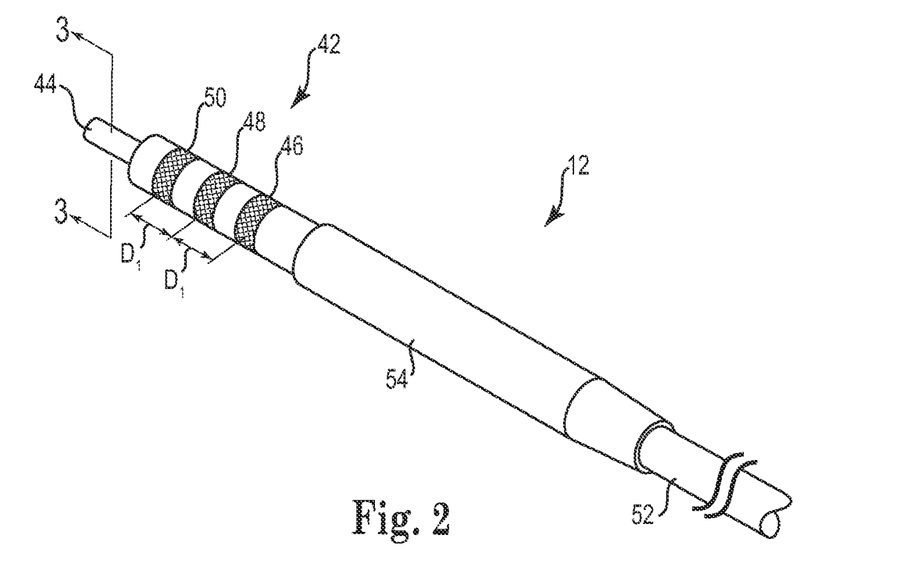
FIG. 2 is a perspective view showing the terminal end of the implantable lead of FIG. 1 in greater detail.

FIG. 2 is a perspective view showing the terminal end 42 of the implantable lead 14 of FIG. 1 in greater detail. As further shown in FIG. 2, the implantable lead 14 includes a lead terminal pin 44 and a number of terminal contacts 46, 48 and 50 each spaced axially apart from each other a distance $D_1$ along the length of the lead body 52. The terminal pin 44 is electrically coupled to a tip electrode 40D, and serves as a cathode for the implantable lead 14. The terminal contacts 46, 48 and 50 are electrically coupled to the electrodes 40A, 40B and 40C, respectively.

Although the implantable lead 14 includes a terminal pin 44 and three terminal contacts 46, 48 and 50, in other embodiments the number and configuration of the terminal contacts may vary from that shown. In one embodiment, for example, the implantable lead 14 may be a bi-polar pacing lead including a single terminal pin and ring electrode. In other embodiments, the implantable lead 14 may be a CRT lead with four low-voltage electrodes. In one such embodiment, for example, the implantable lead 14 may be a VDD or single pass lead having two right ventricle (RV) electrodes and two right atrium (RA) electrodes. In some embodiments, the lead 14 may be an ICD lead. Other lead configurations are also possible.

Figure 3:
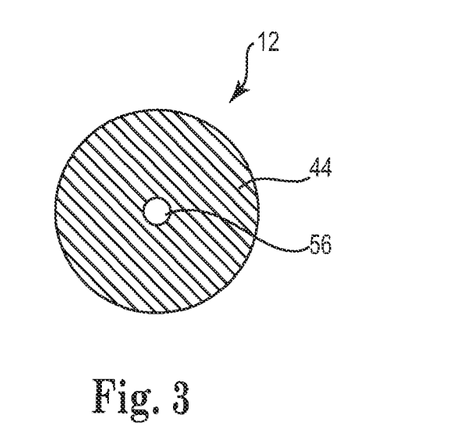
FIG. 3 is a transverse cross-sectional view showing the implantable lead across line 3-3 in FIG. 2.

FIG. 3 is a transverse cross-sectional view showing the implantable lead 14 across line 3-3 in FIG. 2. As further shown in FIG. 3, and in some embodiments, the lead body 52 has a circular cross-sectional shape, and includes an enlarged-diameter terminal boot 54 located distally of the terminal contacts 46, 48 and 50. In certain embodiments, the terminal pin 44 includes a pin lumen 56 sized and shaped to allow various stylets or guidewires to be inserted through the implantable lead 14 during the implantation procedure.

Referring briefly to FIG. 1, the lead evaluation device 34 is shown schematically. In some embodiments, the lead evaluation device 34 may be configured to be pre-loaded onto the implantable lead 14. In some embodiments, the lead evaluation device 34 may be configured to be axially slid onto the terminal end 42 of the lead 14. In some embodiments, the lead evaluation device 34 may be side-loaded onto the lead 14. FIGS. 4-9 provide illustrative but non-limiting examples of particular configurations for the lead evaluation device 34.

Figure 4:
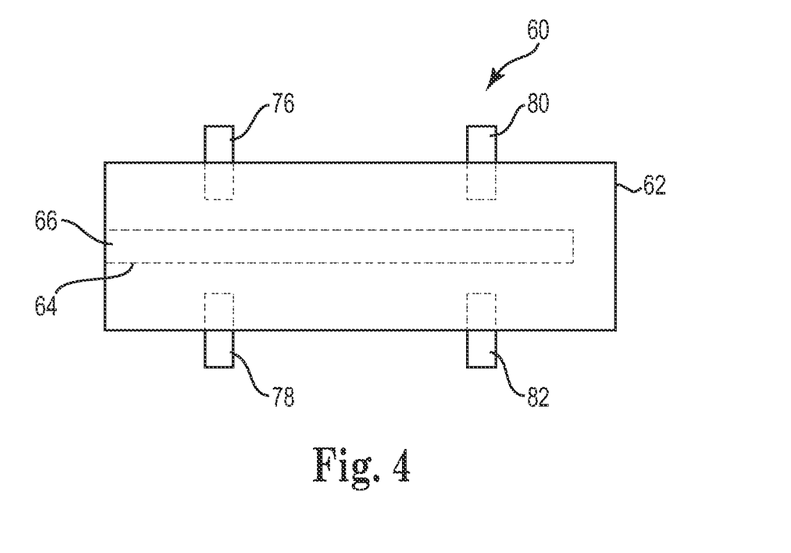
FIG. 4 is a top view of a lead evaluation device in accordance with an embodiment of the present invention.
Figure 5:
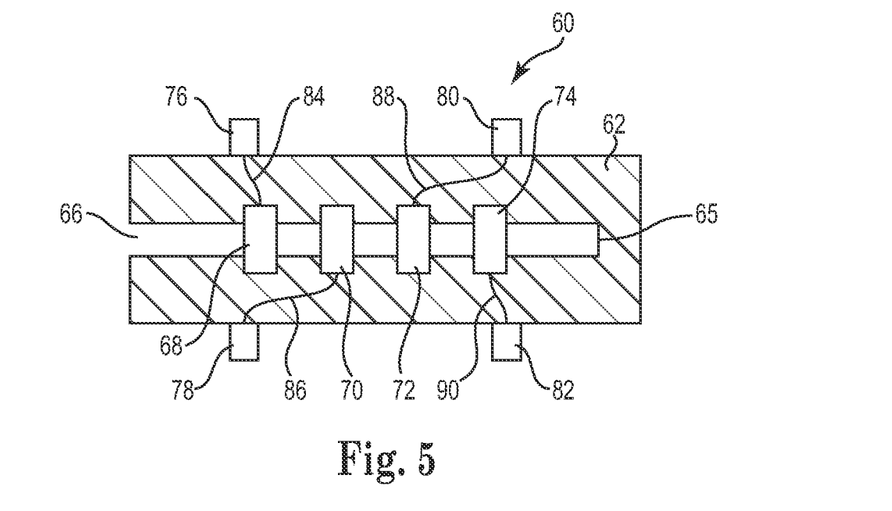
FIG. 5 is a cross-section of the lead evaluation device of FIG. 4.

FIG. 4 is a top view of a lead evaluation device 60 while FIG. 5 is a cross-sectional view of the lead evaluation device 60. The lead evaluation device 60 includes a main body 62 and a channel 64 extending through the main body 62. The channel 64 is sized to accommodate the terminal end 42 of the lead 14 and in some embodiments includes an opening 66 that is sized to frictionally engage the terminal end 40 to releasably secure the lead 14 relative to the lead evaluation device 60. In some embodiments, the channel 64 extends all the way through the main body 62. In some embodiments, as illustrated, the channel 64 extends to a terminus 65. The lead evaluation device 60 includes several ring conductors that may be configured to make electrical contact with the terminal pin 44 and three terminal contacts 46, 48 and 50 yet permit axial loading of the lead evaluation device 60.

In some embodiments, as illustrated in FIG. 5, the lead evaluation device 60 includes three ring conductors 68, 70 and 72 that are sized and positioned to make electrical contact with the terminal contacts 46, 48 and 50. The lead evaluation device 60 also includes a ring conductor 74 that is sized and positioned to make electrical contact with the terminal pin 44. In some embodiments, the ring conductors 68, 70, 72 and 74 may include annular springs that float within a cylindrical housing. The annular springs may have a relaxed configuration in which the springs make contact with the terminal contacts 46, 48 and 50 and/or the terminal pin 44 and yet can easily stretch to permit axial loading and/or unloading of the lead 14 into and/or from the lead evaluation device 60. In some embodiments, the ring conductors 68, 70, 72 and 74 may instead be ring connectors that do not use springs, but rather include resilient contacts as described in commonly owned U.S. Patent Publication No. 2008/0275523, which is incorporated by reference herein.

In some embodiments, the lead evaluation device 60 includes tabs 76, 78, 80 and 82 which are electrically connected to the ring connectors 68, 70, 72 and 74, respectively, by wires 84, 86, 88 and 90. In some embodiments, the tabs 76, 78, 80 and 82 may be configured to accommodate alligator clips or similar structures for electrically connecting the lead evaluation device 60 to the conductors 43 extending back to the PSA 38. As illustrated, the tabs 76, 78, 80 and 82 extend outwardly from the main body 62. In some embodiments, as illustrated in phantom, the tabs 76, 78, 80 and 82 may instead be located within voids formed within the main body 62. In some embodiments, this may better protect the tabs 76, 78, 80 and 82 from accidental damage. Moreover, while this embodiment has been illustrated with tabs 76, 78, 80 and 82, it will be appreciated that in some instances the lead evaluation device 60 may instead include a hardwired cable that plugs directly into the PSA 38 and thus does not require the use of alligator clips or other similar connecting structures.

Figure 6:
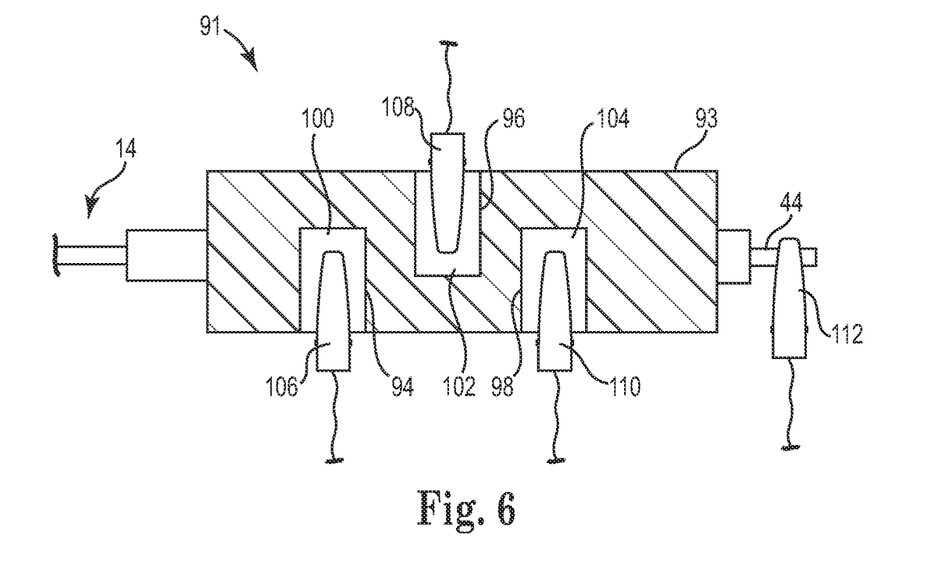
FIG. 6 is a top view of an implantable lead disposed in a lead evaluation device in accordance with an embodiment of the present invention.

FIG. 6 is a top view of lead 14 extending through a lead evaluation device 91 that includes a main body 93. In this embodiment, the main body 93 includes recesses 94, 96 and 98 that are configured and positioned to accommodate several terminal contact clips 100, 102 and 104. The terminal contact clips 100, 102 and 104 are configured and positioned to releasably make electrical contact with the terminal contacts 46, 48 and 50. In some embodiments, the terminal contact clips 100, 102 and 104 are biased to a relaxed configuration in which they do not make physical contact with the lead 14. The terminal contact clips 100, 102 and 104 may be moved into a contact configuration by an externally applied compressive force. In some embodiments, this force may be applied by clamping an alligator clip or similar structure to the terminal contact clips 100, 102 and 104.

In some embodiments, one or more of the terminal contact clips 100, 102 and 104 may be configured to provide electrical contact between one or more of the terminal contacts 46, 48 and 50 any time the lead 14 is disposed within the lead evaluation device 91. For example, in some embodiments, one or more of the terminal contact clips 100, 102 and 104 may be biased towards a position in which the terminal contact clip is in physical contact with the corresponding terminal contact. The terminal contact clip may be sufficiently resilient to permit the lead 14 to move into and out of the lead evaluation device 91. In some embodiments, the terminal contact clip may include structure (not illustrated) that permits electrical contact between the terminal contact and the terminal contact clip regardless of whether an alligator clip is secured to the terminal contact clip.

As illustrated, alligator clips 106, 108 and 110 are clipped onto the terminal contact clips 100, 102 and 104 while an alligator clip 112 is clipped directly to the terminal pin 44. In some embodiments, the terminal pin 44 may be internal to the main body 93, and thus the lead evaluation device 91 would include a terminal pin contact clip (not illustrated) to which the alligator clip 112 could be clipped.

Figure 7:
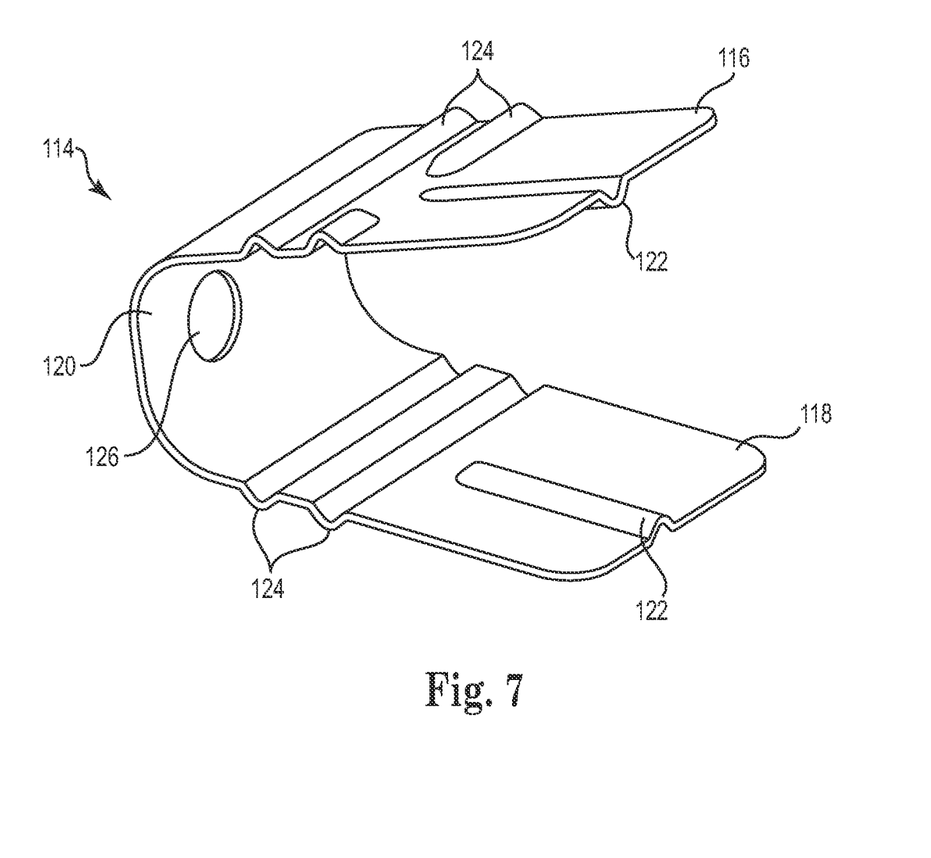
FIG. 7 is a perspective view of a spring contact clip in accordance with an embodiment of the present invention.

FIG. 7 is a perspective view of a spring contact clip 114 that may be used as either a terminal contact clip or a terminal pin contact clip. In some embodiments, the spring contact clip 114 may have a smaller height if used as a terminal pin contact clip. The spring contact clip 114 includes an upper portion 116, a lower portion 118 and an intervening hinge portion 120. Definitions of upper and lower merely refer to the illustrated orientation, as the clip 114 will function in other orientations as well. In some embodiments, as illustrated, the spring contact clip 114 may include one or more internal ridges 122 that provide contact with a terminal contact or terminal pin. The spring clip 114 may also include one or more external ridges 124 that provide better gripping for an alligator clip. In some embodiments, the spring clip 114 may include a mounting aperture 126 that may be used to help anchor the spring clip 114 within a lead evaluation device.

The spring contact clip 114 may be formed of an electrically conductive metal such as MP35N, nickel-plated steel, or nickel-plated beryllium copper, and functions as an intermediate electrical contact to facilitate the transfer of electrical signals back and forth between the PSA conductor 43 and the terminal contacts 46, 48, 50 and/or the terminal pin 44. The relative locations of the internal ridges 122 may be adjusted to accommodate the geometry of a particular lead evaluation device.

Figure 8:
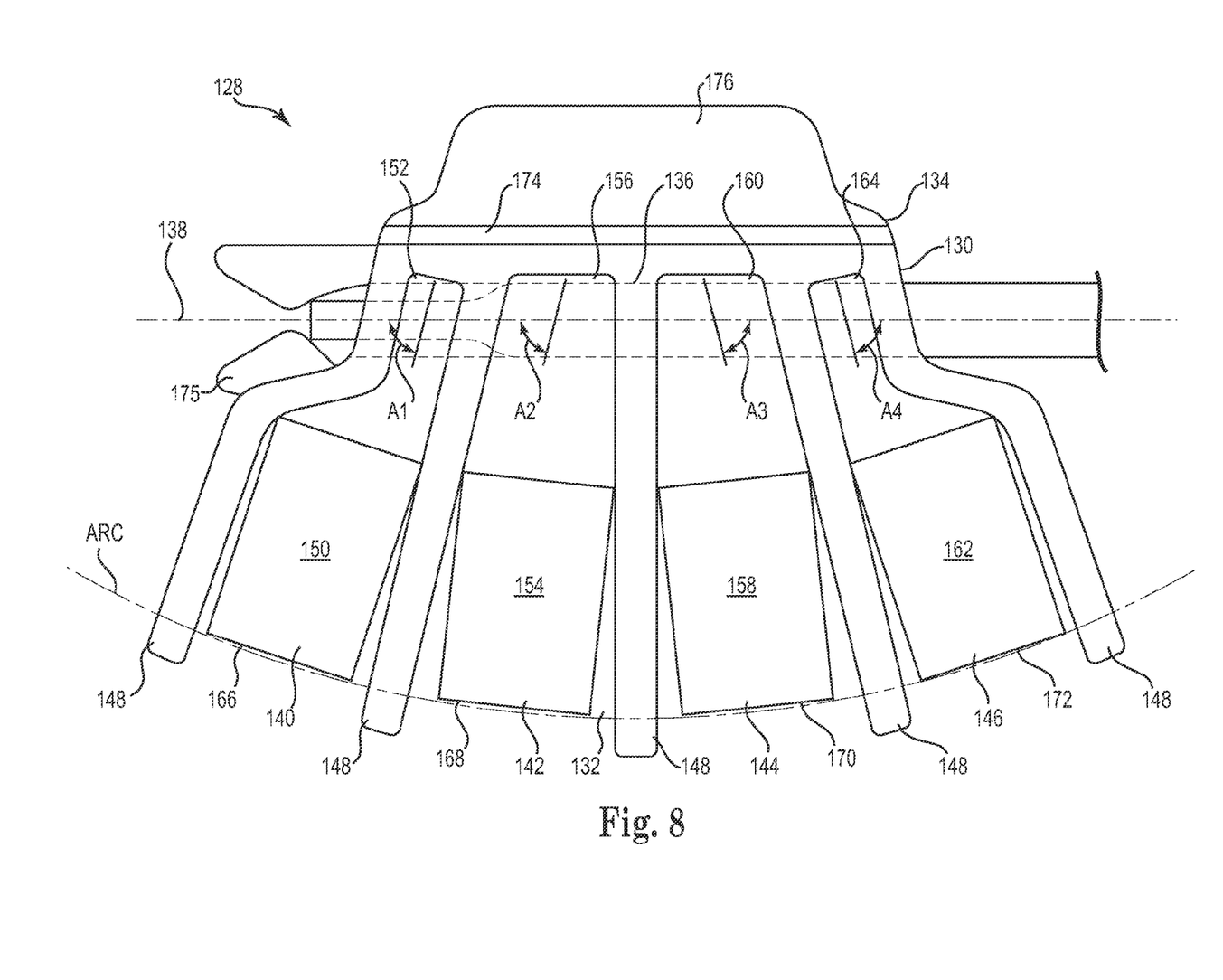
FIG. 8 is a top view of a lead evaluation device in accordance with an embodiment of the present invention.

FIG. 8 is a top view of a lead evaluation device 128 that includes a main body 130. The main body 130 has a curved first side 132 and an opposing second side 134. The main body 130 may be formed of any electrically insulative material such as a non-conducting polymeric material. In some embodiments, the main body 130 may be molded out a polymer such as an acetyl or polypropylene.

A channel 136 that is configured to accommodate the implantable lead 14 extends through the main body 130. The channel 136 may be considered as having a longitudinal axis 138. In the illustrated embodiment, the lead evaluation device 128 includes a terminal pin contact clip 140 and three terminal contact clips 142, 144 and 146. Each of the contact clips 140, 142, 144 and 146 are separated by raised insulation regions 148 that help to locate the contact clips 140, 142, 144 and 146 as well as to help prevent accidental contact between adjacent contact clips and/or the alligator clips or similar structures that are clipped to the contact clips 140, 142, 144 and 146.

The terminal pin contact clip 140 includes an alligator clip engagement portion 150 and a terminal pin engagement portion 152 that is narrower than the alligator clip engagement portion 150. In some cases, having a narrower terminal pin engagement portion 152 reduces interference with adjacent contacts. The terminal pin engagement portion 152 can be seen as defining an acute angle $A_1$ with the longitudinal axis 138.

The terminal contact clips 142, 144 and 146 may be considered as including alligator clip engagement portions 154, 158 and 162, respectively. Similarly, the terminal contact clips 142, 144 and 146 may be considered as having terminal engagement portions 156, 160 and 164, respectively, that are narrower than the corresponding alligator clip engagement portions 154, 158 and 162. The terminal engagement portions 156, 160 and 164 each form acute angles $A_2$, $A_3$ and $A_4$, respectively, with the longitudinal axis 138.

The contact clips 140, 142, 144 and 146 each include hinge portions 166, 168, 170 and 172, respectively. The hinge portions 166, 168, 170 and 172 may be considered as being aligned along an arc labeled ARC that at least substantially matches a curvature of the curved first side 132.

In some embodiments, the lead evaluation device 128 may include an elongate groove 174 that extends along the second side 134 of the main body 130. The elongate groove 174, if present, provides access to the channel 136 extending through the main body 130 and thus permits side-loading of the lead evaluation device 128 onto the stiffening member 15. In some embodiments, the lead evaluation device 128 includes an optional clamping tab 176 that permits a user to temporarily locate the lead evaluation device 128 by, for example, clamping the clamping tab 176 to a surgical drape or other available device or structure.

In some embodiments, the lead evaluation device 128 may include a guide funnel 175 that is either formed as part of the main body 130 or is secured to the main body 130. If present, the guide funnel 175 may assist a user in guiding a stiffening member such as a guidewire or stylet into the lead. In some embodiments, the lead evaluation device 128 may include the elongate groove 174 as well as the guide funnel 175. In some embodiments, the lead evaluation device 128 may include only one or the other. In some embodiments, the lead evaluation device 128 may not include the elongate groove 174 or the guide funnel 175.

The exact dimensions of the contact clips 140, 142, 144 and 146 and the angles $A_1$, $A_2$, $A_3$ and $A_4$ may vary, depending for example on the overall size of the main body 130 and the dimensions of the implantable lead 14. In an illustrative but non-limiting example, $A_1$ and $A_4$ may be about 70.5 degrees while $A_2$ and $A_3$ may be about 83.5 degrees. In this example, the raised insulation regions 148 may have a width of about 0.05 inches. The alligator clip engagement portions 150, 154, 158 and 162 may have a width of about 0.234 inches and a length of about 0.321 inches. The terminal engagement portions 152 and 164 may have a width, measured parallel to the longitudinal axis 138, of about 0.076 inches while the terminal engagement portions 156 and 160 may have a width of about 0.162 inches.

Figure 9:
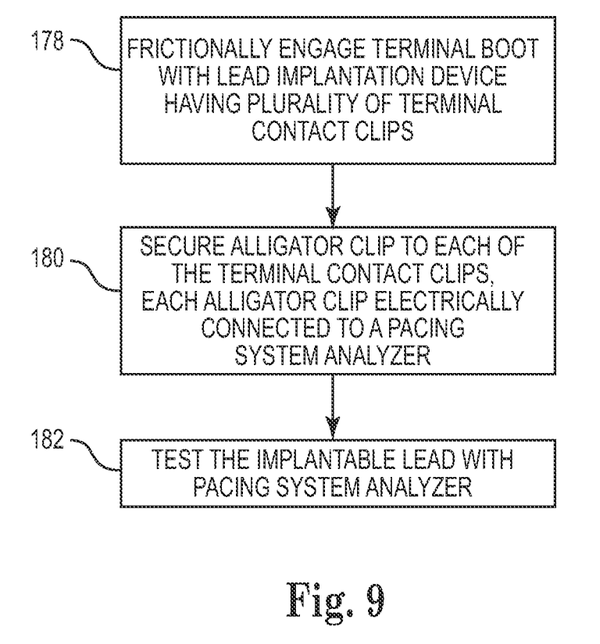
FIG. 9 is a flow diagram illustrating a method of testing an implantable lead in accordance with an embodiment of the present invention.

FIG. 9 is a flow diagram illustrating a method of testing an implantable lead such as the implantable lead 14. The terminal boot of the implantable lead 14 may be frictionally engaged with a lead evaluation device that includes a plurality of terminal contact clips, as generally indicated at block 178. In some embodiments, the terminal boot may be frictionally engaged with the lead evaluation device at the factory, or prior to use. At block 180, an alligator clip that is electrically connected to a pacing system analyzer may be secured onto each of the plurality of terminal contact clips. The implantable lead 14 may then be tested using the pacing system analyzer as generally indicated at block 182.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A lead evaluation device configured for connection to a proximal portion of an implantable lead having a terminal boot, a plurality of terminal contacts and a terminal pin, the lead evaluation device comprising:
   a main body including an opening configured to frictionally engage the terminal boot, the main body including a first side and an opposing second side;
   a channel extending through the main body from the opening, the channel configured to accommodate the proximal portion of the implantable lead including the plurality of terminal contacts; and
   a plurality of terminal contact clips coupled to the main body such that each of the plurality of terminal contact clips, having one or more external ridges extending horizontally along the terminal contact clip and configured to provide a contact for an alligator clip and one or more internal ridges arranged extending vertically along the terminal contact clip, wherein each of the plurality of terminal contact clips are biased into a relaxed configuration and positioned to releasably make electrical contact with a corresponding one of the plurality of terminal contacts via the one or more internal ridges when the implantable lead is disposed within the channel and in response to a force applied by placing the alligator clip.

2. The lead evaluation device of claim 1, further comprising a clamping tab disposed along either the first side or the second side of the main body to permit temporarily fixating the lead evaluation device.

3. The lead evaluation device of claim 1, wherein each of the plurality of terminal contact clips do not extend into the channel and may be moved into a contact configuration in which they extend into the channel and contact the proximal portion of the implantable lead by placing the alligator clip onto each of the plurality of terminal contact clips.

4. The lead evaluation device of claim 1, wherein at least one of the plurality of terminal contact clips are configured to be in contact with at least one of the terminal contacts when the lead is disposed in the channel.

5. The lead evaluation device of claim 1, wherein each of the plurality of terminal contact clips comprise a spring clip including an upper portion, a lower portion and an intervening hinge portion, at least one of the upper portion and the lower portion including a contact ridge for contacting an electrode.

6. The lead evaluation device of claim 1, further comprising a terminal pin contact clip configured to contact the terminal pin when the implantable lead is disposed within the lead evaluation device.

7. The lead evaluation device of claim 1, wherein one or more of the plurality of terminal contact clips are disposed along the first side of the main body and one or more of the plurality of terminal contact clips are disposed along the second side of the body.

8. The lead evaluation device of claim 1, wherein the first side of the main body is curved, the plurality of terminal contact clips are disposed along the first side of the body, and the terminal pin contact clip is disposed along the first side of the body.

9. The lead evaluation device of claim 8, wherein the plurality of terminal contact clips each have a configuration including a relatively wider clamping portion proximate the first side of the main body and a relatively narrower terminal contact portion disposed on an opposing side of the channel from the relatively wider clamping portion.

10. The lead evaluation device of claim 1, further comprising an elongate groove extending along either the first side or the second side of the main body to permit side-loading of the lead evaluation device over a stiffening member.

11. A system for testing an implantable lead within the body of a patient, the system comprising:
   an implantable lead having a terminal boot, a plurality of terminal contacts and a terminal pin;
   a pacing system analyzer electrically connected to a plurality of alligator clips; and
   the lead evaluation device of claim 1, upon which the plurality of alligator clips may be releasably attached for testing the implantable lead.

12. A method of testing an implantable lead during or after implantation, the implantable lead including a terminal boot, a plurality of terminal contacts and a terminal pin, the method comprising:
   frictionally engaging the terminal boot of the implantable lead with a lead evaluation device including:
      a main body including an opening configured to frictionally engage the terminal boot, the main body including a first side and an opposing second side;
      a channel extending through the main body from the opening, the channel configured to accommodate the proximal portion of the implantable lead including the plurality of electrodes; and
      a plurality of terminal contact clips coupled to the main body such that each of the plurality of terminal contact clips, having one or more external ridges extending horizontally along the terminal contact clip and configured to provide a contact for an alligator clip and one or more internal ridges arranged extending vertically along the terminal contact clip, wherein each of the plurality of terminal contact clips are biased into a relaxed configuration and are positioned to releasably make electrical contact with a corresponding one of the plurality of terminal contacts via the one or more internal ridges when the implantable lead is disposed within the channel and in response to a force applied by placing the alligator clip;
   securing an alligator clip onto each of the plurality of terminal contact clips, each of the alligator clips being electrically connected to a pacing system analyzer; and
   testing the implantable lead with the pacing system analyzer.

* * * * *